(12) United States Patent
Burla et al.

(10) Patent No.: US 7,955,265 B2
(45) Date of Patent: Jun. 7, 2011

(54) METHOD AND APPARATUS FOR MEASURING ANATOMIC STRUCTURES

(75) Inventors: Elina Burla, Kiryat Tivon (IL); Doron Hess, Haifa (IL); Alexander Sokulin, Kiryat Tivon (IL)

(73) Assignee: General Electric Company, Schenectady, NY (US)

( * ) Notice: Subject to any disclaimer, the term of this patent is extended or adjusted under 35 U.S.C. 154(b) by 508 days.

(21) Appl. No.: 11/203,904

(22) Filed: Aug. 15, 2005

(65) Prior Publication Data
US 2007/0038084 A1 Feb. 15, 2007

(51) Int. Cl.
*A61B 8/14* (2006.01)
(52) U.S. Cl. .................................. 600/458; 600/437
(58) Field of Classification Search .......... 600/407–481; 382/128
See application file for complete search history.

(56) References Cited

U.S. PATENT DOCUMENTS

| | | | | | |
|---|---|---|---|---|---|
| 4,945,478 | A | * | 7/1990 | Merickel et al. | 382/131 |
| 6,267,728 | B1 | * | 7/2001 | Hayden | 600/481 |
| 6,817,982 | B2 | * | 11/2004 | Fritz et al. | 600/443 |
| 6,996,261 | B2 | * | 2/2006 | deCharms | 382/131 |
| 7,090,640 | B2 | * | 8/2006 | Barth et al. | 600/443 |
| 2003/0199762 | A1 | * | 10/2003 | Fritz et al. | 600/437 |
| 2004/0116808 | A1 | * | 6/2004 | Fritz et al. | 600/437 |
| 2004/0167403 | A1 | * | 8/2004 | Nightingale et al. | 600/437 |
| 2005/0220357 | A1 | * | 10/2005 | Rifu | 382/255 |

OTHER PUBLICATIONS

Martin et al., "Contrast for Vascular Imaging", May 2004, Cardiology Clinics, vol. 22, Issue 2, pp. 313-320.*
Macioch et al., "Effect of contrast enhancement on measurement of carotid artery intimal medial thickness", 2004, Vascular Medicine, 9, pp. 7-12.*
Liguori et al., "An Automatic Measurement System for the Evaluation of Carotid Intima-Media Thickness", Dec. 2001, IEEE Transactions on Instrumentation and Measurement, vol. 50, No. 6, pp. 1684-1691.*
Laurent Belhassen, MD, PHD et al.; Evaluation of Carotid Artery and Aortic Intima-Media Thickness Measurements for Exclusion of Significant Coronary Atherosclerosis in Patients Scheduled for Heart Valve Surgery; Journal of the American College of Cardiology; vol. 39, No. 7, 2002; pp. 1139-1144.
Pamela S. Douglas, MD; Atherosclerosis: It's All in the Arteries; Journal of the American society of Echodardiography, vol. 15 No. 6; pp. 25A-26A, 2002.
Ales Linhart, MD et al.;Carotid Intima-Media Thickness:The Ultimate Surrogate End-Point of Cardiovascular Involvement in Atherosclerosis;Applied Radiology,Mar. 2000, pp. 25-39.

* cited by examiner

*Primary Examiner* — Brian Casler
*Assistant Examiner* — Nasir Shahrestani
(74) *Attorney, Agent, or Firm* — Dean Small; The Small Patent Law Group

(57) ABSTRACT

Methods, apparatus and systems for measuring a thickness of a portion of a multi-layer vessel based on at least one medical diagnostic image frame using an integrated ultrasound device is provided. The method includes for each x-coordinate determining a y-coordinate along an interface between each layer of the vessel including determining a Y coordinate of a center of an intima-media center (IMC) determining the adventitia-media interface Y coordinate, determining the intima-lumen interface Y coordinate, determining for each X coordinate the lumen-intima interface Y coordinate, determining media-adventitia interface Y coordinate, determining a thickness of at least one vessel layer using X and Y coordinates of respective layer interfaces, and outputting the thickness to a display.

44 Claims, 6 Drawing Sheets

METHOD AND APPARATUS FOR MEASURING ANATOMIC STRUCTURES

BACKGROUND OF THE INVENTION

This invention relates generally to medical diagnostic systems. In particular, the present invention relates to methods and apparatus for acquiring and processing diagnostic data sets to identify the location of the transition between different types of tissue and between tissue and blood.

Coronary artery disease (CAD) has many known causes. The early detection and treatment of significant occlusive CAD before infarction is an important goal in reducing the downstream consequences of CAD. Many variables contribute to vascular health and may prove useful in the search for early markers of at-risk individuals. For example, echocardiography has the ability to measure one of the most important of the early markers, atherosclerotic burden. Atherosclerotic burden may be measured crudely during transesophageal echocardiography of the aorta. Further, as usually performed in clinical practice, the detection of plaque is qualitative at best, making it unlikely that robust data can be derived for early detection of preclinical artherosclerosis. Far more carefully studied is high resolution B-mode ultrasound scanning of the carotid arteries with measurement of intima-medial thickness (IMT). This test has been a mainstay of epidemiologic investigations of coronary and cerebrovascular disease for decades. Excellent data document the validity of using carotid findings to predict the state of the coronary circulation, and carotid IMT both detects patients with current disease as well as accurately predicting future cardiac and cerebrovascular events. Carotid IMT measurements have been proven to provide incremental data to traditional risk prediction based on clinical data. It is the only imaging test recommended by the American Heart Association for this purpose. Ultrasound imaging allows precise measurement of the total intima and media thickness of large-and medium-size peripheral arteries like the carotid, femoral, or radial arteries. A known method to measure IMT is based on high-resolution B-mode imaging. Repeated and averaged manual measurement is relatively easy to perform, but is operator-dependent and of poor reproducibility. An accurate measurement with excellent reproducibility can be achieved only by using computer-assisted automatic methods.

However, in some instances it may be difficult to visualize the intima-media structure clearly and measure the IMT under a standard B-mode ultrasound exam. Such difficulties may be caused by technical issues, the presence of plaque buildup, or certain pathology or other disease.

IMT is defined as the distance between the kumen-intima (intima-lumen) interface and the media-adventitia (adventitia-media) interface. Such interfaces are well defined only for posterior wall where there is a clear interface between the anechoic vessel lumen and the echogenic intima, and between the hypoechoic media and the echogenic adventitia. Even when the anterior IMT is well visualized, its measurement remains gain-dependent and unreliable. The proximal IMT measurements are reliable and reproducible only when done on the contrast enhanced images

BRIEF DESCRIPTION OF THE INVENTION

In one embodiment, a method for measuring a thickness of a portion of a multi-layer vessel based on at least one medical diagnostic image frame using an integrated ultrasound device is provided. The method includes for each x-coordinate determining a y-coordinate along an interface between each layer of the vessel including determining a Y coordinate of a center of an intima-media center (IMC) determining the adventitia-media interface Y coordinate, determining the intima-lumen interface Y coordinate, determining for each X coordinate the lumen-intima interface Y coordinate, determining media-adventitia interface Y coordinate, determining a thickness of at least one vessel layer using X and Y coordinates of respective layer interfaces, and outputting the thickness to a display.

In another embodiment, an integrated ultrasound device includes a transmitter for transmitting ultrasound signals into an area of interest, a receiver for receiving echo signals from the transmitted ultrasound signals, a memory for storing at least one image frame including the echo signals, an electrocardiograph gating (ECG) waveform and synchronization unit, a processor configured to process said at least one image frame to automatically identify at least one of a lumen-intima interface and a media adventia interface of a vessel wall, and an output for outputting information based on an output of said processor.

In yet another embodiment, method for measuring a thickness of a portion of a multi-layer vessel is provided. The method includes selecting a region-of-interest (ROI) wherein the ROI includes at least one of an image frame and a portion of an image frame, calculating an intensity histogram of the selected ROI, normalizing image frame intensity values based on the calculated histogram, applying smoothing laterally along the image in a direction of the vessel, and applying a median filter 3×3 to the ROI iteratively wherein the first iteration begins from the upper left pixel of the ROI and every next iteration moves the starting point one pixel down with respect to the x-axis and one pixel to the left with respect to the y-axis. The method also includes determining a shift between an intensity vector corresponding to the x coordinate and an intensity vector corresponding to the x−1 coordinate using a maximum of a cross correlation function, calculated for each x coordinate, determining an Averaged Pattern (AP) and an Inversed Averaged Pattern (IAP) using an average along the x-axis of all intensity vectors into the ROI, taking into account shift between the neighbor vectors wherein the AP is evaluated in the ascending direction of x-axis and the IAP is evaluated in the descending direction of x-axis, and determining a shift between the AP and the first vector in the ROI using a maximum of a cross correlation function between the AP with the first vector in the ROI. The method further includes determining a shift between the IAP and the last vector in the ROI using a maximum of a cross correlation function between the LAP with the last vector in the ROI, determining the Y coordinate of the intima-media center (IMC) as a maximum of the second derivative of the AP/IAP wherein if the ROI includes anterior and posterior adventitia, the anterior IMC is determined as a global maximum on the first half of the vector of the second derivative of the AP/IAP and the posterior IMC is found as a global maximum on the second half of the vector of the second derivative of the AP/IAP, if the ROI includes only anterior or posterior adventitia, the IMC is determined as a global maximum on the whole vector of the second derivative of the AP/IAP. The method further includes determining a Running Pattern (RP) and the Inversed Running Pattern (IRP) for each X coordinate wherein the running pattern is calculated for each X coordinate as an average along the x-axis of the intensity vectors inside the window of the specific Window Size (WS), taking into account shift between the neighbor vectors, the RP is evaluated in the ascending direction of the x-axis, the IRP is evaluated in the descending direction of the x-axis, determining for each X coordinate, a Running Shift (RS) between the ROI vector and the RP corresponding to the current X coordinate and Averaged Shift (AS) between the ROI vector corresponding to the current X coordinate and the AP wherein the RS and the AS are determined as a maximum of the cross correlation function between the ROI vector and RP and AP respectively, for the first WS vectors of the ROI, the RS and the AS are found as a maximum of the cross correlation function between the ROI vector and IRP and IAP respectively, determining, for each X coordinate, the Y coordinate of the center of intima-media as a maximum of the second derivative of the RP or IRP corresponding to the current X coordinate wherein for the first WS vectors of the ROI, applying the IRP, for the remaining vectors in the ROI, applying the RP, and determining for each X coordinate, the adventitia-media interface Y coordinate as the coordinate of the nearest zero crossing previous to the anterior IMC coordinate found on the second derivative of the RP or IRP corresponding to the each X coordinate. The method also includes determining for each X coordinate the intima-lumen interface Y coordinate as the coordinate of the nearest zero crossing after the anterior IMC coordinate found on the second derivative of the RP or IRP corresponding to the each X coordinate, determining for each X coordinate the lumen-intima interface Y coordinate as the coordinate of the nearest zero crossing previous to the posterior IMC coordinate found on the second derivative of the RP or IRP corresponding to the each X coordinate, and determining for each X coordinate media-adventitia interface Y coordinate as the coordinate of the nearest zero crossing after the posterior IMC coordinate found on the second derivative of the RP or IRP corresponding to the each X coordinate.

DETAILED DESCRIPTION OF THE INVENTION

In instances when the anterior IMT should be measured or it is difficult to visualize the posterior intima clearly under a standard B-mode ultrasound exam because of, for example, technical issues, the presence of plaque buildup, or certain pathology or other disease, contrast-enhanced B-mode ultrasound imaging of the vessel's walls are performed by administering a bolus of intravenous contrast agent for ultrasound, and scanning the contrast-filled vessel with a scanner that has been optimized for this mode of imaging. This method permits quantification of the aggregate mean intima-media thickness (IMT) of the near and far wall of the carotid or any other vessel containing contrast agent.

Figure 1:
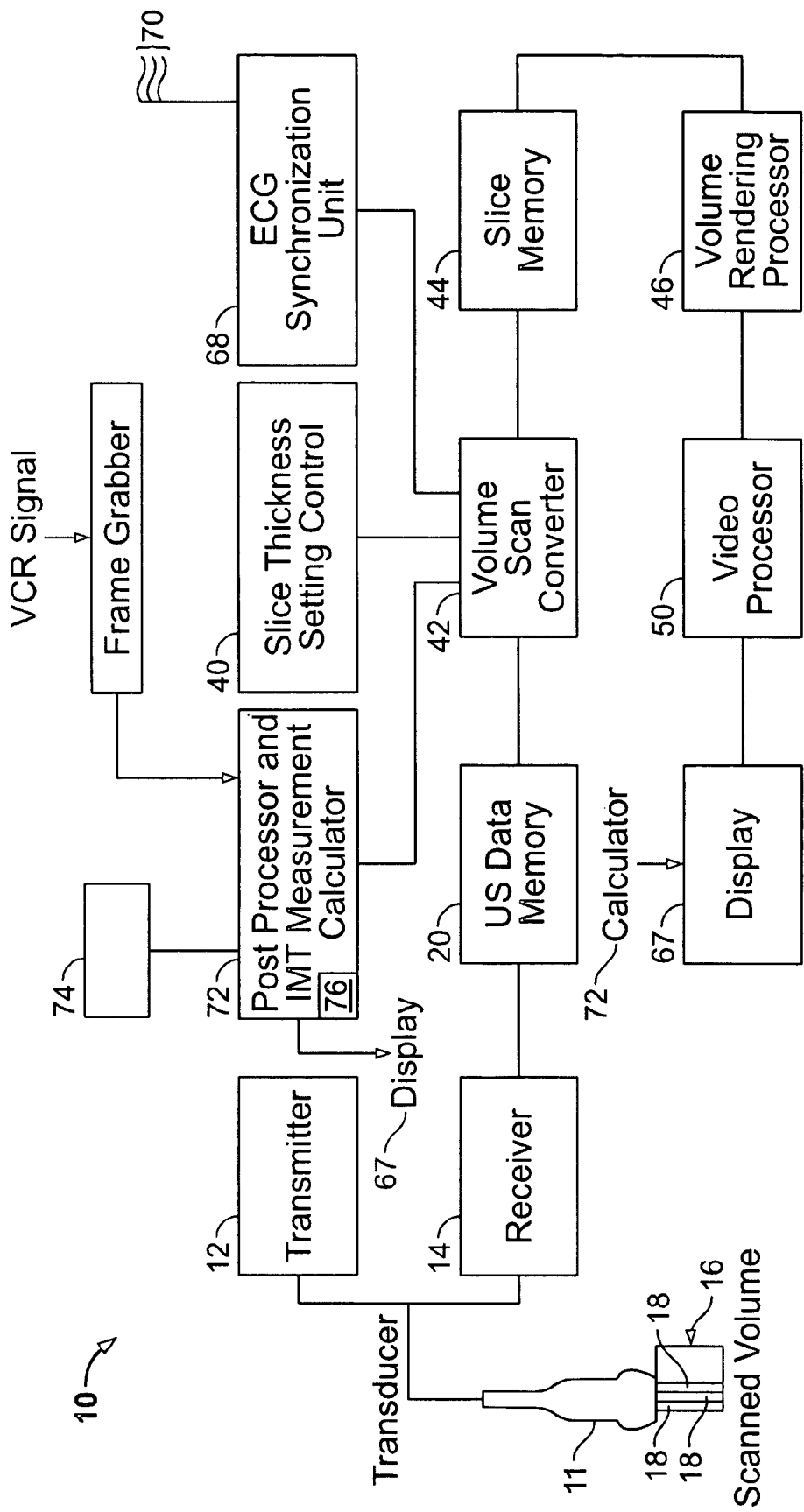
FIG. 1 is a block diagram of an ultrasound system constructed in accordance with an embodiment of the present invention.

FIG. 1 is a block diagram of an ultrasound system constructed in accordance with an embodiment of the present invention. The system includes a transducer 11 connected to a transmitter 12 and a receiver 14. The transducer 11 transmits ultrasonic pulses and receives echoes from structures inside of a scanned ultrasound image or volume 16. Memory 20 stores ultrasound data from the receiver 14 derived from the scanned ultrasound image or volume 16. The image or volume 16 may be obtained by various techniques (e.g., 3D scanning, real-time 3D imaging, volume scanning, 2D scanning with transducers having positioning sensors, freehand scanning using a voxel correlation technique, 2D or matrix array transducers and the like).

Transducer 11 is moved, such as along a linear or arcuate path, while scanning a region of interest (ROI). The scan planes 18 are stored in the memory 20, and then passed to a scan converter 42. Scan-converter 42 synchronizes the modules of ultrasound system 10. In some embodiments, the transducer 11 may obtain lines instead of the scan planes 18, and the memory 20 may store lines obtained by the transducer 11 rather than the scan planes 18. The scan converter 42 may store lines obtained by the transducer 11 rather than the scan planes 18. The scan converter 42 creates a data slice from a single scan plane 18. The data slice is stored in slice memory 44 and then passed to the video processor 50 and display 67. System 10 may facilitate measuring an anatomic structure within the region of interest in at least one of a real-time mode, a frame freeze mode, a cine-loop run mode, a VCR playback mode, and an ultrasound device internal archive single frame or loop frame playback mode.

An integral ECG waveform and synchronization unit 68 is coupled to a patient skin (not shown). ECG waveform and synchronization unit 68 uses a plurality of electrodes 70 to measure electrical current passing through a patient's body. The electrical current corresponds to the electrical activity of the patient's heart muscles, or the contraction and relaxation thereof. This current is used to identify a cyclical portion of the heart's cycle, thus allowing blood-vessel data to be acquired during intervals that substantially correspond to a substantially similar portion of the heart's cycle when the blood vessel is in a substantially uniform position. An automatic border-detection and measurement tool embodied in a post-processor and intima-media thickness measurement calculator 72 may receive raw image data and/or scan converted data to identify structures of a blood vessel and automatically determine thicknesses of those structures. Post-processor and intima-media thickness measurement calculator 72 may also receive archive data from a data archive 74, such as a video cassette recorder (VCR) and/or a VCR play-back internal frame grabber unit, or other data storage device, which is located locally to system 10, integral with system 10, or is located remotely from system 10 and accessed over a data network (not shown). Post-processor and intima-media thickness measurement calculator 72 may transmit highlighting signals to display 67 to provide trace determined interfaces with a brighter pixel intensity and/or false color highlight of determined interfaces to aid an operator in determining accurate output. Post-processor and intima-media thickness measurement calculator 72 also transmits, for example, a tracing of the lumen-intima and the media-adventitia interfaces, an average IMT value based upon all of the points that were detected, a standard deviation of all the IMT value measurements, additional values derived from the measurements data-set, such as a maximal point, and a minimal point.

Additionally, a graph is selectably positioned to display the value of the IMT as function of location along the vessel, or as function of time inside a heart cycle and is selectably based on a single frame, or averaged on several heart cycles using synchronization with ECG to peak images from a specific heart-cycle point. The above outputs are fed into display unit 67 and are merged with the original image, for the user to view and approve. The user assigns the name of the anatomical site where the measurement has been made (i.e. Left Common Carotid) and views the automatic tracing of the intima-media lines and the rest of the above information and then approves or disapproves of the results. If the user approves the results being displayed on the screen, the values that were displayed will be placed into a measurements database in the patient's exam folder in archiving unit 74. The set of values will be assigned and associated with the anatomical location that was previously defined by the user. If the user disapproves the results they are erased, allowing the user to re-measure or exit from the measurement function. The result-screen with the above IMT information overlay, including the traces can be stored into archiving unit 74 for later retrieval. When measurement values and images are saved into archiving unit 74, a report-generation unit 76 selectably generates a full report by using a predetermined prepared report template to display the measurements, saved images and other user's comments. In the exemplary embodiment, report-generation unit 76 is illustrated as being a portion of calculator 72. In an alternative embodiment, report-generation unit 76 is a separate unit or part of another unit of system 10.

A user-adjustable sensitivity parameter varies the sensitivity of the algorithm to noise or soft tissue in a real-time scan, or on a frozen or retrieved loop to improve the delineation of the structures by correct location of the tracing as the operator perceives it. Such adjustment permits the user to improve image quality degraded by soft-plaque or other artifacts. The user-adjustable sensitivity parameter also permits adjustment to a level that facilitates delineation of the borders of the plaque in order to measure plaque thickness rather than IMT thickness alone.

System 10 can synchronize on any part of the ECG waveform arriving from built-in ECG unit 68 or from an external ECG waveform. The synchronization location is presetable and automatic, but can also be manually adjusted. To facilitate repeatable results the IMT measurement is performed at a fixed point in time relative to the ECG waveform, such as during end-diastolic.

Synchronization is selected by the user to be based on vessel-wall motion detection or on ECG waveform. The same IMT algorithm is used, in this case, to delineate both walls of vessel (anterior and posterior). By measuring the wall's distance as function of time it is possible to follow the pulsatility of the vessel, and synchronize the frame-selection for IMT measurement in similar fashion as the synchronization to the ECG waveform.

When acquiring a loop, the IMT calculation is performed on different frames along the heart-cycle, to display an instant set of measurements for each time division, relative to the synchronization waveform. The points of time-division are presetable by the user. This, for example, allows automatic calculation of intima-media or plaque thickness contractility or elasticity.

During a relatively long cine-loop that includes N heart-cycles a multi-slice mode is used to average the IMT at specific points in time relative to synchronization waveform over a number of loops in order to increase accuracy.

Images used for measurement can be "raw-data" ultrasound images, or processed by a special noise-reduction technique (for example SRI (speckle reduction imaging)).

Figure 2:
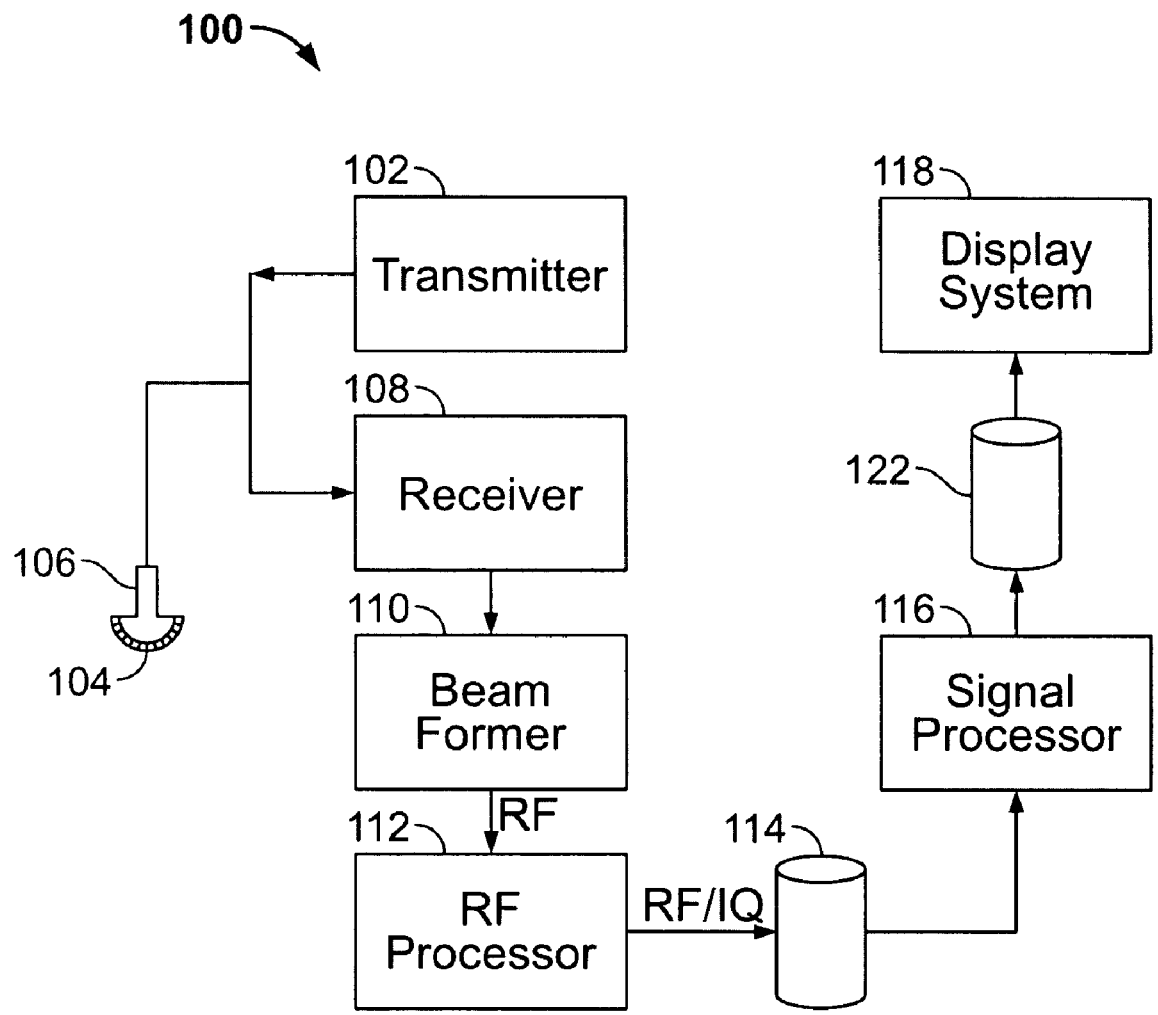
FIG. 2 is a block diagram of an exemplary ultrasound system constructed in accordance with another embodiment of the present invention.

FIG. 2 is a block diagram of an exemplary ultrasound system constructed in accordance with another embodiment of the present invention. The ultrasound system 100 includes a transmitter 102, which drives an array of elements 104 within a transducer 106 to emit pulsed ultrasonic signals into a body. A variety of geometries are used. The ultrasonic signals are back-scattered from structures in the body, like blood cells or muscular tissue, to produce echoes, which return to the elements 104. The echoes are received by a receiver 108. The received echoes are passed through a beamformer 110, which performs beamforming and outputs an RF signal. The RF signal then passes through an RF processor 112. Alternatively, the RF processor 112 may include a complex demodulator (not shown) that demodulates the RF signal to form IQ data pairs representative of the echo signals. The RF or IQ signal data may then be routed directly to RF/IQ buffer 114 for temporary storage.

The ultrasound system 100 also includes a signal processor 116 to process the acquired ultrasound information (i.e., RF signal data or IQ data pairs) and prepare frames of ultrasound information for display on display system 118. The signal processor 116 is adapted to perform one or more processing operations according to a plurality of selectable ultrasound modalities on the acquired ultrasound information. Acquired ultrasound information is processed in real-time during a scanning session as the echo signals are received. Additionally, or alternatively, the ultrasound information is stored temporarily in RF/IQ buffer 114 during a scanning session and processed in less than real-time in a live or off-line operation.

The ultrasound system 100 may continuously acquire ultrasound information at a frame rate that exceeds fifty frames per second, which is the approximate perception rate of the human eye. The acquired ultrasound information is displayed on the display system 118 at a slower frame-rate. An image buffer 122 is included for storing processed frames of acquired ultrasound information that are not scheduled to be displayed immediately. The image buffer 122 is of sufficient capacity to store at least several seconds worth of frames of ultrasound information. The frames of ultrasound information are stored in a manner to facilitate retrieval thereof according to its order or time of acquisition. The image buffer 122 may comprise any known data storage medium.

Figure 3:
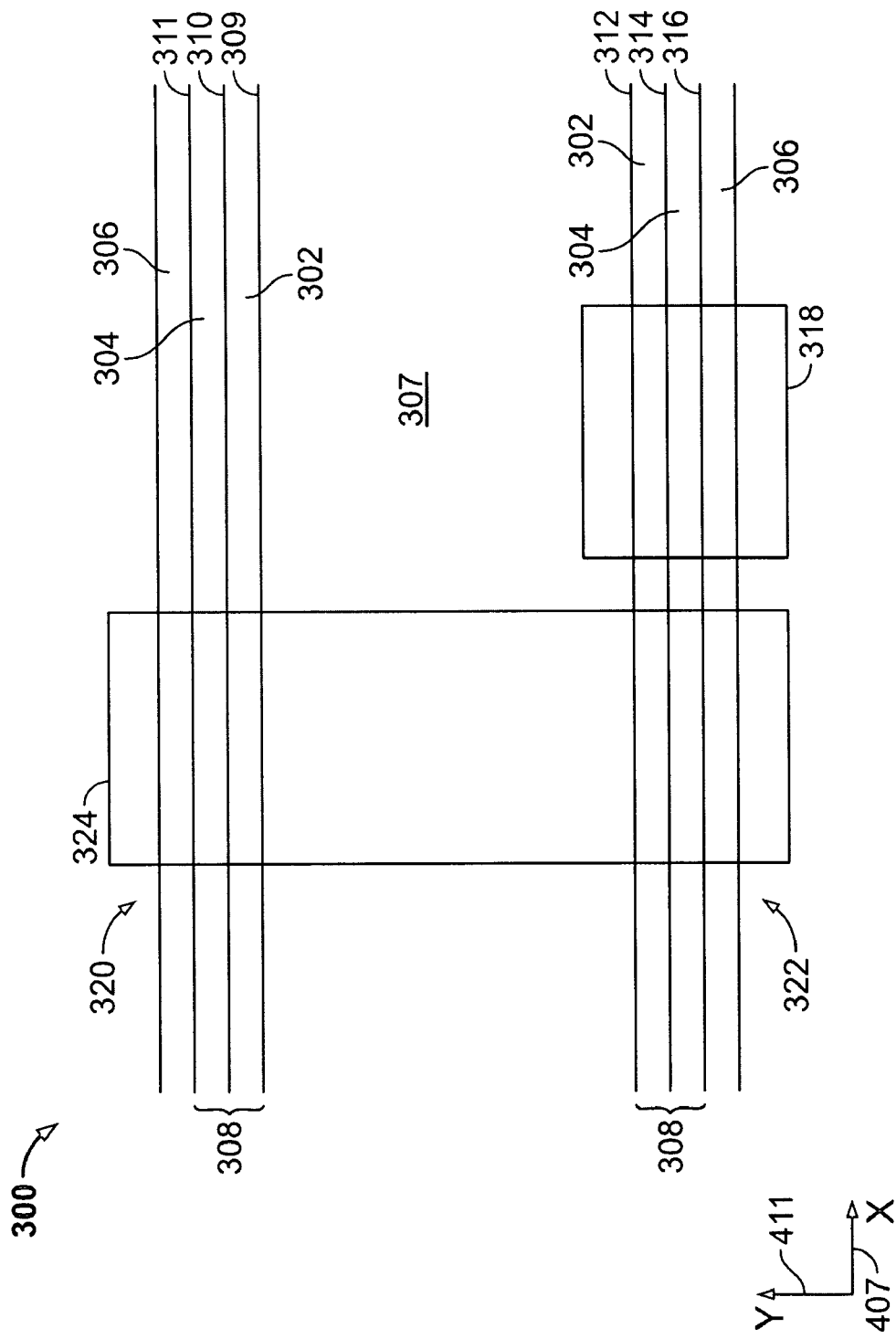
FIG. 3 is a schematic view of a longitudinal cross-section of an exemplary artery that may be scanned using the ultrasound system shown in FIG. 1.

FIG. 3 is a schematic view of a longitudinal cross-section of an exemplary artery 300 that may be scanned using ultrasound system 10 shown in FIG. 1. In the exemplary embodiment, artery 300 includes three layers, a tunica intima 302, a media 304, and adventitia 306 that define a tubular cavity therein referred to as a lumen 307. At least some known diseases may cause one or more of such layers to thicken and/or obtain a plaque coating. For example, tunica intima 302 or media 304 may thicken due to a lesion. Specifically, arterial sclerosis may cause intima 302 to thicken. Further, hypertension may cause media 304 to thicken. Accordingly, respective diseases are evaluated by measuring the thickness of intima 302, the thickness of media 304 or a combined measurement of an intima-medial thickness (IMT) 308. To facilitate measuring thicknesses of the various layers, an interface between the layers is used, such as, for example, on an anterior side of artery 300, a lumen-intima interface 309, a intima-media interface 310, and a media-adventitia interface 311, and on a posterior side of artery 300, a lumen-intima interface 312, a intima-media interface 314, and a media-adventitia interface 316.

In some instances the anterior IMT should be measured or it is difficult to visualize the posterior intima clearly under a standard B-mode ultrasound exam. In such instances, contrast-enhanced B-mode ultrasound image of the vessel's walls is acquired. A bolus of intravenous contrast agent for ultrasound is administered to the patient, and the contrast-filled vessel is scanned with a scanner that has been optimized for this mode of imaging. This method allows quantification of the aggregate mean intimal medial thickness (IMT) of the near and far wall of the carotid or any other vessel containing contrast agent.

When scanning a vessel including contrast, the automatic border-detection and measurement tool permits accurate and reproducible identification and measurement of the combined thickness of the intimal and medial layers, including any wall thickening, plaque formation, and lumen enlargement due to residual plaque and the vasa vasorum network found within the adventitial/media/intima regions of the arteries.

During a scan, a user selects a region of interest (ROI) 318 that includes a portion of an anterior wall 320 and/or a portion of a posterior wall 322 of a vessel, such as artery 300. A user may select a second ROI 324 that includes both a portion of anterior wall 320 and a portion of posterior wall 322 of the vessel, if the scan is to be performed using tissue motion synchronization. Tissue motion synchronization and electro-cardiograph gating (ECG) synchronization permits evaluation of frames captured at a fixed time relative to an oscillatory motion of a tissue, such as, a vein or artery wall, and heart wall, at a fixed time relative to a heart cycle. In the exemplary embodiment, the IMT measurement is performed at a selectable fixed point in time relative to the ECG waveform, for example, during end-diastole. System 10 can synchronize on any part of the ECG waveform received from the built-in ECG unit or from an external ECG waveform. The synchronization location is preselectable and automatic, but is manually adjusted.

The synchronization discussed above is selected by a user to be based on vessel-wall motion detection rather than on ECG waveform. The same automatic border-detection and measurement tool algorithm is used, in this case, to delineate both walls of artery 300 (anterior 320 and posterior 322). By measuring the distance between anterior wall 320 and posterior wall 322 as function of time, it is possible to follow the pulsatility of artery 300, and synchronize the frame-selection for an IMT measurement similarly to the synchronization to the ECG waveform.

System 10 may receive image data at a resolution greater than display is capable of displaying. For example system 10 is able to obtain images with a 1200 pixel per inch resolution, but display 67 may only be capable of displaying 400 pixels per inch. System 10 may use the display resolution images to measure IMT and may selectably zoom display 67 to use the entire 1200 pixel per inch resolution available in the received image. Such a zoom feature facilitates an accurate IMT measurement. System 10 also configured to detect a zoom setting for each frame of image data, for example, live data, archived data, and frame grabbed data from a VCR playback. A user may retrieve image frame data from a plurality of image frame data sources, such as real-time data raw data, real-time data preprocessed data, frame freeze data, cine-loop data, and/or VCR playback data. When reviewing image frame data from various sources collected at widely varying time-frames, each image frame is stored in different resolution setting with respect to each other image frame. Correlating image frames over time is used while making a diagnosis, such that viewing image frames at different resolution settings may cause errors to be made. System 10 may selectably read the resolution setting and zoom setting of each image frame and automatically modify the resolution setting and/or zoom setting of each image frame to be consistent with respect to each other at a user-preferred selectable setting.

In various embodiments, to facilitate imaging and the determination of the vessel IMT, a contrast agent is injected into the vessel prior to or during a scan. Generally, contrast is injected into the blood-stream passing through the vessel, such as artery 300, to facilitate enhancing visibility of the blood vessels and the vessel-borders delineation. The contrast agent also may enhance the visibility and delineation of "soft-plaque", which is non-reflective (i.e., has very dark gray shade) and is difficult to distinguish from the surrounding blood filled lumen. The contrast agent facilitates sound reflection of the blood, such that the blood appears as a lighter gray shade and the relatively darker soft-plaque becomes more distinguishable and visible in the ultrasound image.

Figure 4:
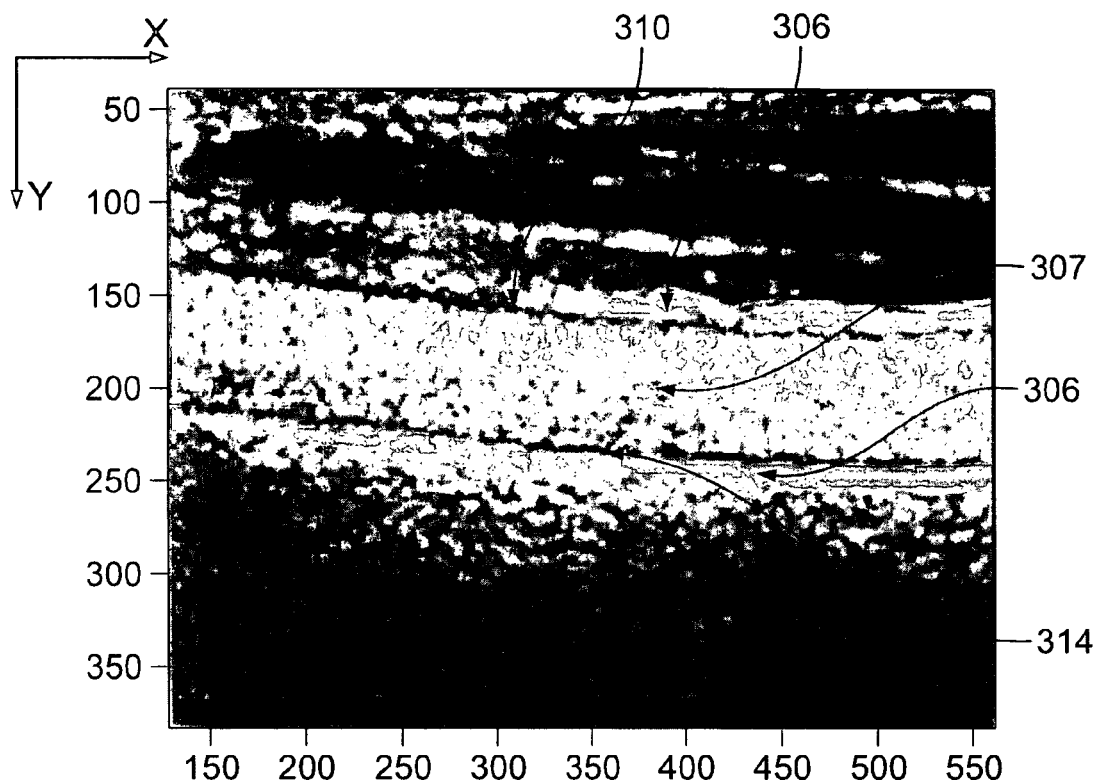
FIG. 4 is an exemplary contrast-enhanced gray-scale image produced from raw ultrasound data that is acquired by the system shown in FIG. 1.

FIG. 4 is an exemplary gray-scale image 400 produced from raw ultrasound data that is acquired by system 10 (shown in FIG. 1). Image 400 is generated from raw ultrasound data after scan-conversion, raw data before scan-conversion, or from any pixel-data image containing visible intima-media 310 and 314 pattern, a low intensity region that separates two high intensity areas, such as lumen 307, including contrast, and adventitia 306.

Figure 5:
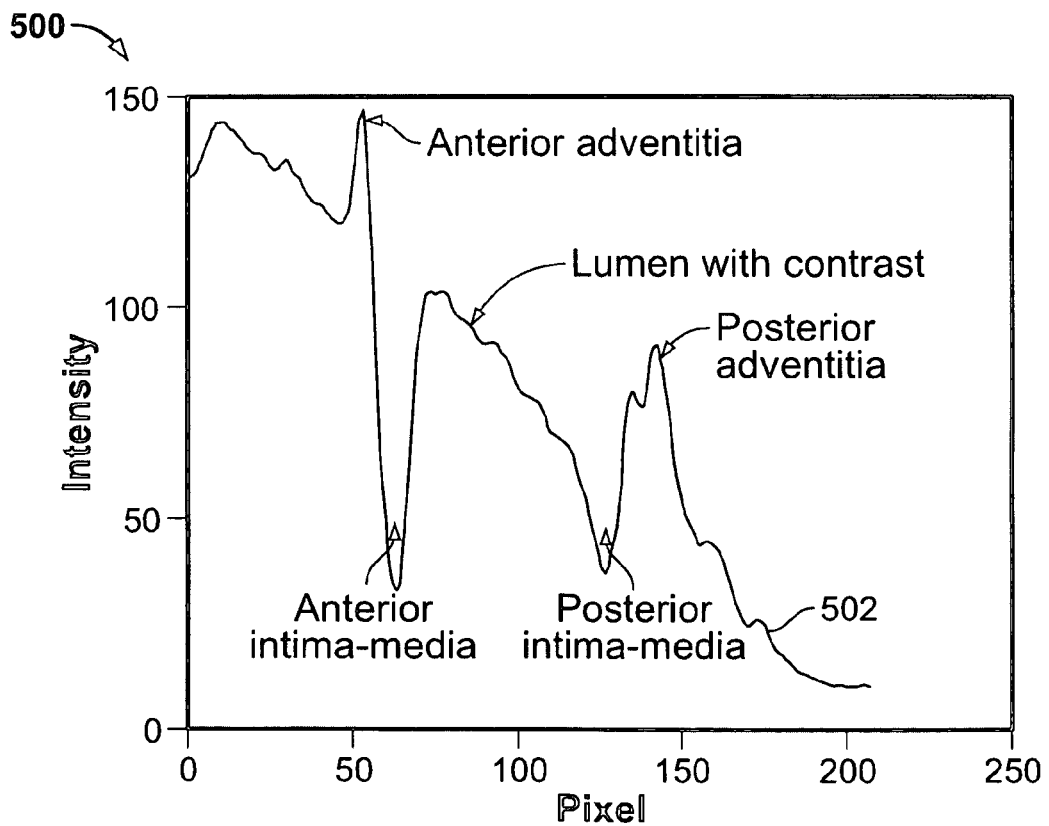
FIG. 5 is a graph of an exemplary trace of an Averaged Pattern (AP) that includes an anterior adventitia and a posterior adventitia.

FIG. 5 is a graph 500 of an exemplary trace 502 of an Averaged Pattern (AP) that in the exemplary embodiment includes an anterior adventitia 504 and a posterior adventitia 506. The averaged pattern is calculated as an average along the x-axis of all intensity vectors into the ROI, taking into account shift between the neighbor vectors. The AP is evaluated in the ascending direction of x-axis.

Figure 6A:
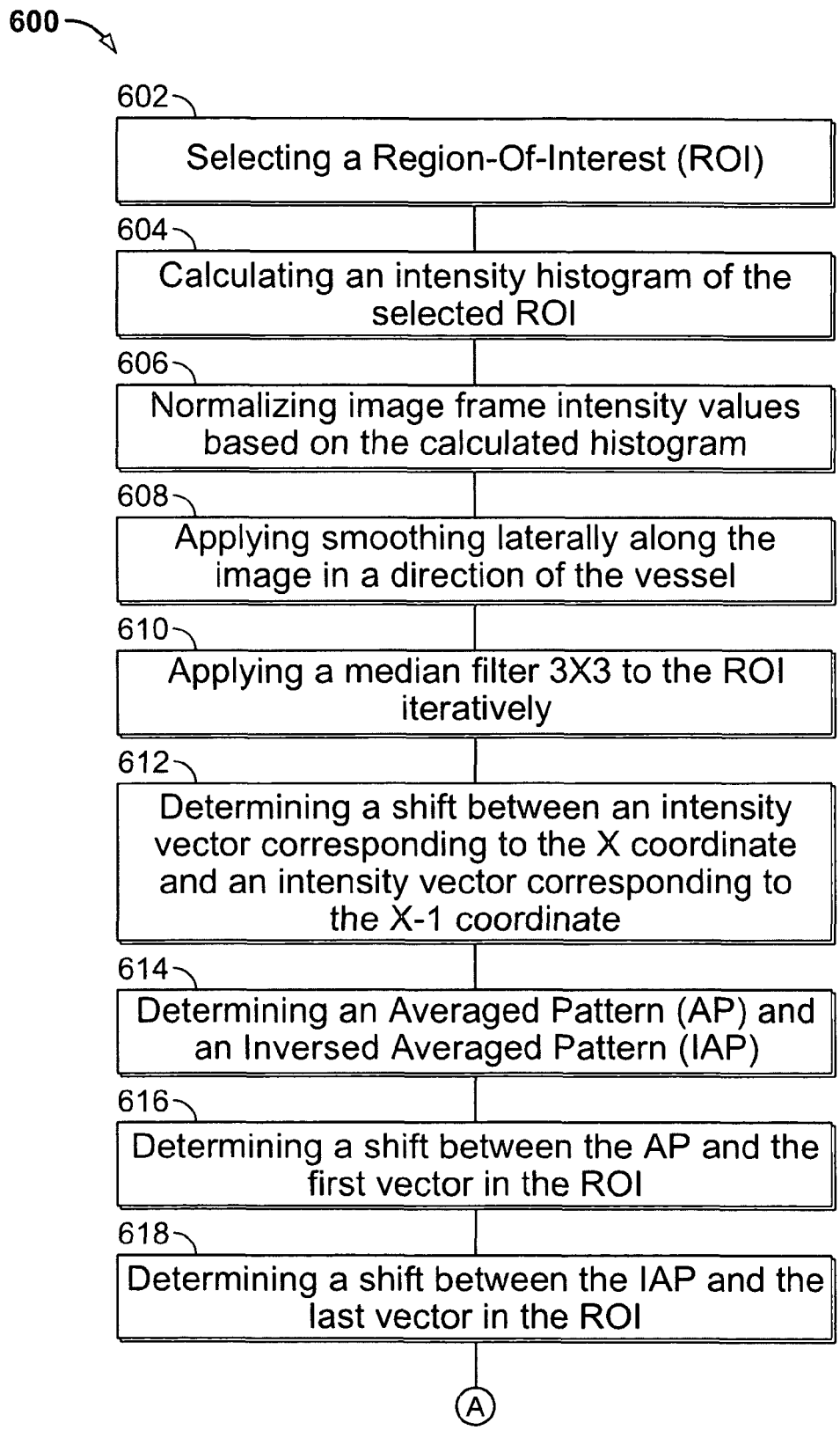
FIG. 6 illustrates an exemplary method for automatic measurement of the aggregate mean IMT from a 2D image of a blood vessel filled with ultrasound contrast agent.
Figure 6B:
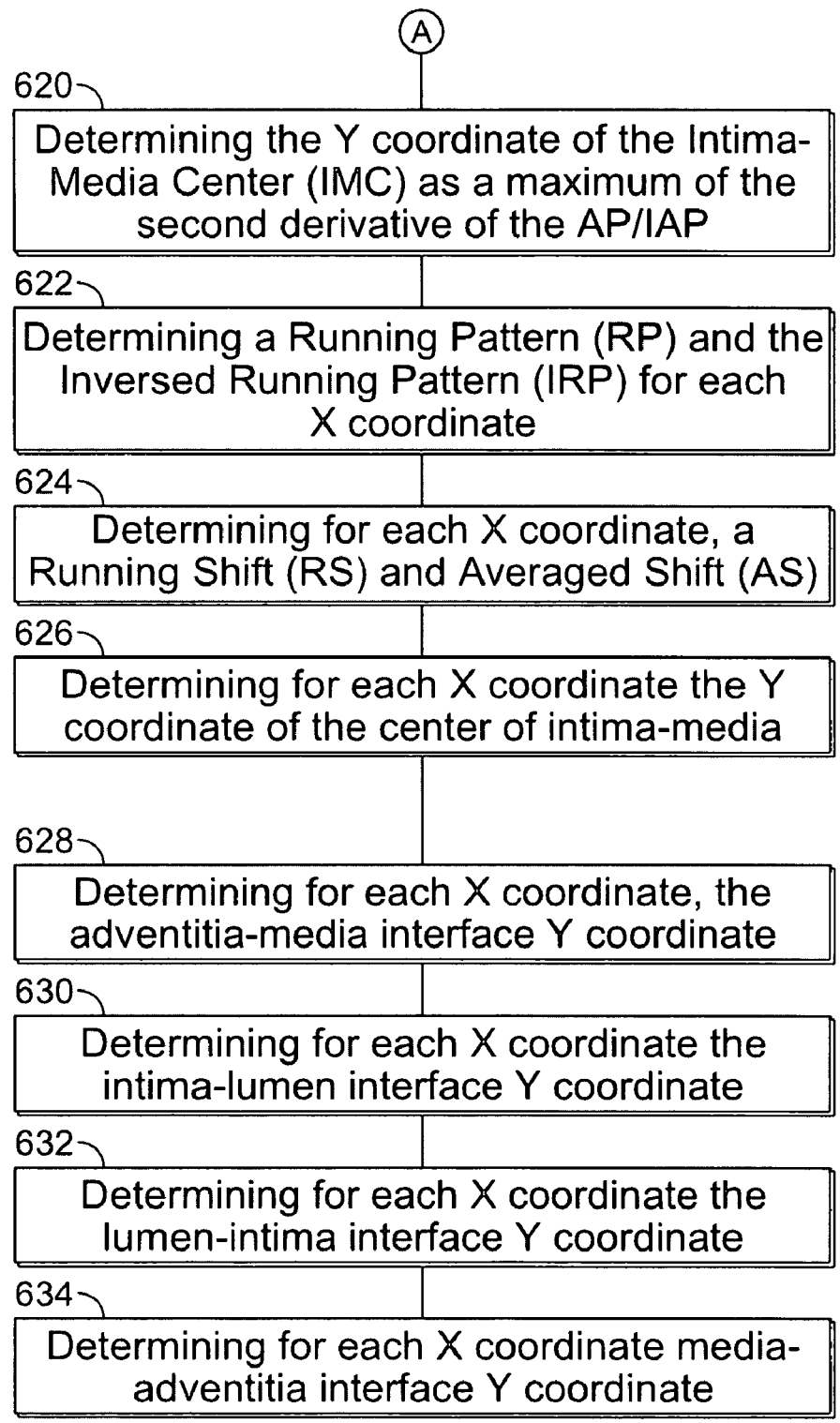

FIG. 6 illustrates an exemplary method 600 for automatic detection of lumen-intima and media-adventitia interfaces. A process or algorithm of method 600 uses an image produced from raw ultrasound data by scan-conversion, or can be applied to raw data before scan-conversion, or is applied to any pixel-data image, for example, a pixel-data image that includes a visible double-line intima-media pattern. Method 600 includes injection of a contrast agent into the blood vessel to facilitate enhancing visibility and delineation of the vessel walls. When using a contrast agent, a plurality of initialization parameters is modified or additional parameters set to indicate to the IMT algorithm that a contrast agent is being used and the characteristics relative to the particular contrast agent used.

Method 600 includes selecting 602 a region-of-interest (ROI) wherein the ROI includes at least one of an image frame and a portion of an image frame and calculating 604 an intensity histogram of the selected ROI. A user selected ROI should include a part of lumen 307 and adventitia 306 (shown in FIG. 3). Image frame intensity values are normalized 606 based on the calculated histogram. Smoothing using, for example, a finite impulse response (FIR) filter is applied 608 laterally along the image in a direction of an artery, such as artery 300 (shown in FIG. 3), for example, an x-axis that is selected relative to an orientation of artery 300. The orientation of the x-axis is independent of the orientation of the artery as viewed in a display. In the exemplary embodiment, the orientation of the artery corresponds to a horizontal x-axis, such as axis 407. In other embodiments, the artery is oriented in any direction with respect to the x-axis.

A median filter 3×3 is applied 610 to the extracted ROI iteratively, the first iteration begins from the upper left pixel of the ROI and every next iteration moves the starting point one pixel down with respect to the x-axis and one pixel to the left with respect to the y-axis. A shift between the vectors (along the vessel's direction, i.e. x-axis in the vessel shown in FIG. 4) is determined 612 as a maximum of the cross correlation function, calculated for each x coordinate, between the intensity vector corresponding to the x coordinate and the intensity vector corresponding to (x−1) coordinate.

An Averaged Pattern (AP) and an Inversed Averaged Pattern (IAP) are determined 614. The AP and IAP may contain one or both anterior and posterior adventitia. The pattern is calculated as an average along the x-axis of all intensity vectors into the ROI, taking into account shift between the neighbor vectors. The AP is evaluated in the ascending direction of x-axis. The IAP is evaluated in the descending direction of x-axis. A shift between the AP and the first vector in the ROI is determined 616 and the shift between the IAP and the last vector in the ROI is determined 618 as a maximum of the cross correlation function between the AP/IAP with the first or last vector in the ROI respectively.

The Y coordinate of the intima-media center (IMC) is determined 620 as a maximum of the second derivative of the AP/IAP. When the ROI contains both anterior and posterior adventitia the anterior IMC is determined 620 as a global maximum on the first half of the vector of the second derivative of the AP/IAP and the posterior IMC is found as a global maximum on the second half of the vector of the second derivative of the AP/IAP. If the ROI contains only anterior or posterior adventitia the center of intima-media is found as a global maximum on the whole vector of the second derivative of the AP/IAP. The Running Pattern (RP) and the Inversed Running Pattern (IRP) for each X coordinate is determined 622. The running pattern is calculated for each X coordinate as an average along the x-axis of the intensity vectors inside the window of the specific Window Size (WS), taking into account shift between the neighbor vectors. The RP is evaluated in the ascending direction of x-axis. The IRP is evaluated in the descending direction of x-axis.

For each X coordinate the Running Shift (RS) between the ROI vector and the RP corresponding to the current X coordinate and Averaged Shift (AS) between the ROI vector corresponding to the current X coordinate and the AP are determined 624. The RS and the AS are found as a maximum of the cross correlation function between the ROI vector and RP and AP respectively. For the first WS vectors of the ROI the RS and the AS are found as a maximum of the cross correlation function between the ROI vector and IRP and IAP respectively. For each X coordinate the Y coordinate of the center of intima-media as a maximum of the second derivative of the RP or IRP corresponding to the current X coordinate is determined 626. For the first WS vectors of the ROI the IRP is applied, for the rest of the vectors in the ROI the RP is applied. When the ROI contains both anterior and posterior adventitia the anterior IMC is found as a global maximum on the first half of the vector of the second derivative of the RP or IRP and the posterior IMC is found as a global maximum on the second half of the vector of the second derivative of the RP or IRP. If the ROI contains only anterior or posterior adventitia the IMC is found as a global maximum on the whole vector of the second derivative of the IP/IRP. A search of the global maximum is done recursively, until one of the following conditions is true.

1) The difference between the coordinate of the IMC, found on the RP or IRP corresponding to the current X coordinate and corrected by RS, and coordinate of the IMC found on the AP or IAP and corrected by AS, less than certain value;
2) The difference between the coordinate of the IMC, found on the RP or IRP corresponding to the current X coordinate and the coordinate of the IMC, found on the RP or IRP corresponding to the (X−1) coordinate, less than certain value.

If neither of these conditions are true, the value of global maximum is substituted by zero and search continues.

For each X coordinate the adventitia-media interface Y coordinate is determined 628 as the coordinate of the nearest zero crossing previous to the anterior IMC coordinate found on the second derivative of the RP or IRP corresponding to the each X coordinate. For each X coordinate the intima-lumen interface Y coordinate is determined 630 as the coordinate of the nearest zero crossing after the anterior IMC coordinate found on the second derivative of the RP or IRP corresponding to the each X coordinate.

For each X coordinate the lumen-intima interface Y coordinate is determined 632 as the coordinate of the nearest zero crossing previous to the posterior IMC coordinate found on the second derivative of the RP or IRP corresponding to the each X coordinate. For each X coordinate media-adventitia interface Y coordinate is determined 634 as the coordinate of the nearest zero crossing after the posterior IMC coordinate found on the second derivative of the RP or IRP corresponding to the each X coordinate.

A technical effect of various embodiments of the present invention is to automatically identify and measure an anatomical structure, such as a blood vessel wall in a vessel including a contrast agent. Specifically, the system captures image frames of ultrasound data representing a region of interest. In one embodiment of the present invention, structures of a blood vessel including a contrast agent are located, identified, and measured. Various methods of displaying the output of the structure and measurements are selectable to facilitate diagnosis.

While various embodiments the present invention have been described with reference to an integrated ultrasound scanner configured to automatically measure IMT in a blood vessel, numerous other applications are contemplated. It is contemplated that the method and systems of the present invention is applied to other imaging modalities, such as MRI, and anatomic structure other than a blood vessel.

The above-described systems and methods of automatically quantifying the aggregate mean IMT of the near and far wall of a vessel containing contrast agent using an integrated ultrasound scanner are cost-effective and highly reliable for facilitating monitoring and diagnosing disease. More particularly, the methods and systems described herein facilitate identifying and determining a thickness of, for example, blood vessel walls with an integrated ultrasound scanner. As a result, the methods and systems described herein facilitate reducing healthcare costs in a cost-effective and reliable manner.

Exemplary embodiments of real-time integrated ultrasound systems and methods are described above in detail. However, the systems are not limited to the specific embodiments described herein, but rather, components of each system is utilized independently and separately from other components described herein. Each system component also can be used in combination with other system components.

While the invention has been described in terms of various specific embodiments, those skilled in the art will recognize that the invention can be practiced with modification within the spirit and scope of the claims.

What is claimed is:

1. A method for measuring a thickness of a portion of a multi-layer vessel based on at least one contrast-enhanced medical diagnostic image frame using an integrated ultrasound device, wherein the at least one image frame including an X-axis that is substantially parallel to an intima-media of the anatomic structure and a Y-axis that is perpendicular to the x-axis, said method comprising:

acquiring an ultrasound image of a portion of the multi-layer vessel wherein the vessel includes ultrasound contrast agents; and automatically determining an intima-medial thickness (IMT) of the contrast enhanced image using an algorithm executing in the integrated ultrasound device and that comprises;

determining an Averaged Pattern (AP) and an Inversed Averaged Pattern (IAP) of a plurality of intensity vectors using an average of the plurality of intensity vectors along the x-axis wherein the AP is evaluated in the ascending direction of x-axis and the IAP is evaluated in the descending direction of x-axis;

determining a Y coordinate of a center of an intima-media center (IMC) of the vessel using a maximum of the second derivative of the AP/IAP wherein if a region of interest (ROI) includes anterior and posterior adventitia, the anterior IMC is determined as a global maximum on the first half of the vector of the second derivative of the AP/IAP and the posterior IMC is found as a global maximum on the second half of the vector of the second derivative of the AP/IAP, if the ROI includes only anterior or posterior adventitia, the IMC is determined as a global maximum on the whole vector of the second derivative of the AP/IAP;

determining a Running Pattern (RP) and an Inversed Running Pattern (IRP) for each X coordinate wherein the running pattern is calculated for each X coordinate as an average along the x-axis of the intensity vectors inside the window of the specific Window Size (WS), taking into account shift between the neighbor vectors, the RP is evaluated in the ascending direction of the x-axis, the IRP is evaluated in the descending direction of the x-axis;

determining for each X coordinate, a Running Shift (RS) between the ROI vector and the RP corresponding to the current X coordinate and Averaged Shift (AS) between the ROI vector corresponding to the current X coordinate and the AP wherein the RS and the AS are determined as a maximum of the cross correlation function between the ROI vector and RP and AP respectively, for the first WS vectors of the ROI, the RS and the AS are found as a maximum of the cross correlation function between the ROI vector and IRP and IAP respectively;

determining, for each X coordinate, the Y coordinate of the center of intima-media as a maximum of the second derivative of the RP or IRP corresponding to the current X coordinate wherein for the first WS vectors of the ROI, applying the IRP, for the remaining vectors in the ROI, applying the RP;

determining for each X coordinate, the adventitia-media interface Y coordinate as the coordinate of the nearest zero crossing previous to the anterior IMC coordinate found on the second derivative of the RP or IRP corresponding to the each X coordinate;

determining for each X coordinate the intima-lumen interface Y coordinate as the coordinate of the nearest zero crossing after the anterior IMC coordinate found on the second derivative of the RP or IRP corresponding to the each X coordinate;

determining for each X coordinate the lumen-intima interface Y coordinate as the coordinate of the nearest zero crossing previous to the posterior IMC coordinate found on the second derivative of the RP or IRP corresponding to the each X coordinate;

determining for each X coordinate media-adventitia interface Y coordinate as the coordinate of the nearest zero crossing after the posterior IMC coordinate found on the second derivative of the RP or IRP corresponding to the each X coordinate;

determining a thickness of at least one vessel layer using X and Y coordinates of respective layer interfaces; and outputting the thickness to a display.

2. A method in accordance with claim 1 further comprising:
administering a contrast agent to the vessel to be imaged; and
modifying at least one of an initialization parameter indicative of the contrast agent used.

3. A method in accordance with claim 1 further comprising:
selecting the ROI wherein the ROI includes at least one of an image frame and a portion of an image frame;
calculating an intensity histogram of the selected ROI; and
normalizing image frame intensity values based on the calculated histogram.

4. A method in accordance with claim 1 further comprising applying a median filter 3×3 to the ROI iteratively wherein the first iteration begins from the upper left pixel of the ROI and every next iteration moves the starting point one pixel down with respect to the x-axis and one pixel to the left with respect to the y-axis.

5. A method in accordance with claim 1 further comprising determining a shift between an intensity vector corresponding to the x coordinate and an intensity vector corresponding to the x−1 coordinate using a maximum of a cross correlation function, calculated for each x coordinate.

6. A method for measuring a thickness of a portion of a multi-layer vessel based on at least one contrast-enhanced medical diagnostic image frame using an integrated ultrasound device, said method comprising:
acquiring, with the integrated ultrasound device, an ultrasound image of a portion of a multi-layer cardiac vessel wherein the vessel includes ultrasound contrast agents;
automatically determining an intima-medial thickness (IMT) of the contrast enhanced image using an algorithm executing in the integrated ultrasound device, the automatically determining comprising:
determining a shift between an Averaged Pattern (AP) and a first vector in a region of interest (ROI) using a maximum of a cross correlation function between the AP with the first vector in the ROI; and
determining a shift between an Inversed Averaged Pattern (IAP) and a last vector in the ROI using a maximum of a cross correlation function between the IAP with the last vector in the ROI; and
outputting the IMT to a display.

7. A method in accordance with claim 1 further comprising:
coupling an ECG waveform and synchronization unit to a patient wherein the ECG waveform and synchronization unit is integral to the integrated ultrasound device; and
transmitting heart cycle information from the patient to a processor of the integrated ultrasound device.

8. A method in accordance with claim 7 further comprising automatically synchronizing the at least one image frame with a selectable portion of at least one of said heart cycle information and an external ECG waveform.

9. A method in accordance with claim 1 further comprising altering the resolution of the at least one image frame to facilitate measuring the IMT of the multi-layers of the vessel.

10. A method in accordance with claim 1 further comprising measuring an anatomic structure in at least one of a real-time mode, a frame freeze mode, a cine-loop run mode, a VCR playback mode, and an ultrasound device internal archive single frame or loop frame playback mode.

11. A method in accordance with claim 1 further comprising processing at least one of raw data ultrasound image frames and preprocessed ultrasound image frames.

12. A method in accordance with claim 1 further comprising displaying an IMT measurement output that includes at least one of a tracing of the lumen-intima interface, a tracing of the media-adventitia interface, an average IMT value based upon a selectable plurality of determined lumen-intima interface points and media-adventitia interface points, a standard deviation of an IMT value measurement, an IMT value measurement maximal point, an IMT value measurement minimal point, a graph of the IMT value measurement as function of location along a vessel, a graph of the IMT value measurement as function of time inside a heart cycle, and derived statistical values for the displayed lumen-intima interface and/or the media-adventitia interface curves.

13. A method in accordance with claim 12 further comprising displaying at least one image frame concurrently with at least one respective IMT measurement on the same display.

14. A method in accordance with claim 1 further comprising:
prompting a user for a signal indicative of approval or disapproval of the output; and
if the signal indicates approval, saving the output of the processor to an integrated ultrasound device archiving unit.

15. A method in accordance with claim 1 wherein the outputting the thickness to a display comprises outputting automatic image display calibration information for the at least one image frame.

16. A method in accordance with claim 1 further comprising receiving a selectable sensitivity adjustment signal wherein the sensitivity adjustment signal facilitates reducing at least one of circuit noise, soft plaque response, artifact response, and soft tissue response.

17. A method in accordance with claim 1 further comprising receiving a selectable sensitivity adjustment signal to delineate one or more plaque borders for measuring a plaque thickness.

18. A method in accordance with claim 1 further comprising:
retrieving a plurality of archived image frames from different scans taken over a predetermined period of time;
determining a zoom setting of each image frame;
modifying a zoom setting of each image frame to a user-preferred selectable setting; and
measuring a change in the IMT of the vessel over the period of time.

19. An integrated ultrasound device comprising:
a transmitter for transmitting ultrasound signals into an area of interest;
a receiver for receiving echo signals from the transmitted ultrasound signals;
a memory for storing at least one image frame including the echo signals;
an electro-cardiograph gating (ECG) waveform and synchronization unit;
a processor configured to:
acquire an ultrasound image of a portion of a multi-layer vessel wherein the vessel is a cardiac vessel that includes ultrasound contrast agents; and
automatically determine an intima-medial thickness (IMT) of the contrast enhanced image using an algorithm executing on the processor, the algorithm configured to determine an Averaged Pattern (AP) and an Inversed Averaged Pattern (IAP) using an average along an x-axis of all intensity vectors into an ROI within the contrast enhanced image, taking into account shift between neighbor vectors, wherein the AP is evaluated in an ascending direction of the x-axis and the IAP is evaluated in a descending direction of the x-axis; and
an output for transmitting the determined IMT.

20. An integrated ultrasound device in accordance with claim 19 wherein said processor is further configured to automatically synchronize image frame selection with a selectable portion of at least one of said heart cycle information and an external ECG waveform.

21. An integrated ultrasound device in accordance with claim 19 wherein said processor is further configured to highlight at least one of a lumen-intima interface and a media-adventia interface.

22. An integrated ultrasound device in accordance with claim 21 wherein said processor is further configured to:
calculate an intensity histogram of a region of interest of the at least one image wherein said image is referenced to a Cartesian coordinate system;
determine an adventitia centerline using said intensity histogram and an average intensity of the adventitia calculated using said intensity histogram;
highlight a media-adventia interface based on a boundary of the determined adventitia;
determine a second axis value of the lumen-intima interface corresponding to a first axis value of the adventia; and
highlight the lumen-intima interface.

23. An integrated ultrasound device in accordance with claim 19 wherein said output is configured to display said contrast enhanced image concurrently with said IMT measurements.

24. An integrated ultrasound device in accordance with claim 19 wherein said processor is further configured to:
prompt a user for a signal indicative of approval or disapproval of the output; and
if the signal indicates approval, the output of said processor is saved to an integrated ultrasound device archiving unit.

25. An integrated ultrasound device in accordance with claim 19 wherein said processor is further configured to identify said at least one of a lumen-intima interface and a media adventia interface based on at least one of a single frame, averaged over a plurality of frames, and averaged over a plurality of frames synchronized at a selectable specific heart-cycle point.

26. An integrated ultrasound device in accordance with claim 19 wherein said output includes automatic image display calibration information.

27. An integrated ultrasound device in accordance with claim 19 wherein said processor is further configured to:
receive an input relative to a contrast agent being used during the scan; and
modify at least one of an initialization parameter indicative of the contrast agent used.

28. A method for measuring a thickness of a portion of a multi-layer vessel based on at least one medical diagnostic image frame using an integrated ultrasound device, the at least one image frame including an x-axis that is oriented along a bottom edge of the image frame substantially parallel to an intima-media of the anatomic structure and a y-axis that is oriented along a leftmost edge and perpendicular to the first axis, said method comprising:

selecting a region-of-interest (ROI) wherein the ROI includes at least one of an image frame and a portion of an image frame;

calculating an intensity histogram of the selected ROI;

normalizing image frame intensity values based on the calculated histogram;

applying smoothing laterally along the image in a direction of the vessel;

applying a median filter 3×3 to the ROI iteratively wherein the first iteration begins from the upper left pixel of the ROI and every next iteration moves the starting point one pixel down with respect to the x-axis and one pixel to the left with respect to the y-axis;

measuring a thickness of a portion of a multi-layer vessel by:

determining a shift between an intensity vector corresponding to the x coordinate and an intensity vector corresponding to the x−1 coordinate using a maximum of a cross correlation function, calculated for each x coordinate;

determining an Averaged Pattern (AP) and an Inversed Averaged Pattern (IAP) using an average along the x-axis of all intensity vectors into the ROI, taking into account shift between the neighbor vectors wherein the AP is evaluated in the ascending direction of x-axis and the IAP is evaluated in the descending direction of x-axis;

determining a shift between the AP and the first vector in the ROI using a maximum of a cross correlation function between the AP with the first vector in the ROI;

determining a shift between the IAP and the last vector in the ROI using a maximum of a cross correlation function between the IAP with the last vector in the ROI;

determining the Y coordinate of the intima-media center (IMC) as a maximum of the second derivative of the AP/IAP wherein if the ROI includes anterior and posterior adventitia, the anterior IMC is determined as a global maximum on the first half of the vector of the second derivative of the AP/IAP and the posterior IMC is found as a global maximum on the second half of the vector of the second derivative of the AP/IAP, if the ROI includes only anterior or posterior adventitia, the IMC is determined as a global maximum on the whole vector of the second derivative of the AP/IAP;

determining a Running Pattern (RP) and the Inversed Running Pattern (IRP) for each X coordinate wherein the running pattern is calculated for each X coordinate as an average along the x-axis of the intensity vectors inside the window of the specific Window Size (WS), taking into account shift between the neighbor vectors, the RP is evaluated in the ascending direction of the x-axis, the IRP is evaluated in the descending direction of the x-axis;

determining for each X coordinate, a Running Shift (RS) between the ROI vector and the RP corresponding to the current X coordinate and Averaged Shift (AS) between the ROI vector corresponding to the current X coordinate and the AP wherein the RS and the AS are determined as a maximum of the cross correlation function between the ROI vector and RP and AP respectively, for the first WS vectors of the ROI, the RS and the AS are found as a maximum of the cross correlation function between the ROI vector and IRP and IAP respectively;

determining, for each X coordinate, the Y coordinate of the center of intima-media as a maximum of the second derivative of the RP or IRP corresponding to the current X coordinate wherein for the first WS vectors of the ROI, applying the IRP, for the remaining vectors in the ROI, applying the RP;

determining for each X coordinate, the adventitia-media interface Y coordinate as the coordinate of the nearest zero crossing previous to the anterior IMC coordinate found on the second derivative of the RP or IRP corresponding to the each X coordinate;

determining for each X coordinate the intima-lumen interface Y coordinate as the coordinate of the nearest zero crossing after the anterior IMC coordinate found on the second derivative of the RP or IRP corresponding to the each X coordinate;

determining for each X coordinate the lumen-intima interface Y coordinate as the coordinate of the nearest zero crossing previous to the posterior IMC coordinate found on the second derivative of the RP or IRP corresponding to the each X coordinate; and determining for each X coordinate media-adventitia interface Y coordinate as the coordinate of the nearest zero crossing after the posterior IMC coordinate found on the second derivative of the RP or IRP corresponding to the each X coordinate.

29. A method in accordance with claim 28 wherein selecting at least one of an image frame and an ROI comprises selecting at least one of an image frame and an ROI that includes a lumen and at least a portion of at least one of an anterior adventitia and a posterior adventitia.

30. A method in accordance with claim 28 wherein applying smoothing comprises applying a finite impulse response (FIR) filter.

31. A method in accordance with claim 28 wherein determining for each X coordinate the Y coordinate of the center of intima-media further comprises:

for the first WS vectors of the ROI, applying the IRP; and
for the remaining vectors in the ROI, applying the RP.

32. A method in accordance with claim 31 further comprising determining a global maximum on the first half of the vector of the second derivative of the RP or IRP and the posterior IMC is found as a global maximum on the second half of the vector of the second derivative of the RP or IRP when the ROI contains both anterior and posterior adventitia the anterior IMC, if the ROI includes only anterior or posterior adventitia, determining the IMC as a global maximum on the whole vector of the second derivative of the IP/IRP.

33. A method in accordance with claim 28 further comprising determining the global maximum recursively, until at least one of:

1) a difference between a coordinate of the IMC, found on the RP or the IRP corresponding to the current X coordinate and corrected by the RS, and a coordinate of the IMC found on the AP or the IAP and corrected by the AS is less than a certain value; and 2) a difference between a coordinate of the IMC, found on the RP or the IRP corresponding to the current X coordinate and a coordinate of the IMC, found on the RP or the IRP corresponding to the (X−1) coordinate, is less than a certain value.

34. A method for measuring a thickness of a portion of a multi-layer cardiac vessel based on at least one medical diagnostic image frame using an integrated ultrasound device, said method comprising:

selecting a region-of-interest (ROI) comprising at least one of an image frame and a portion of an image frame acquired using the integrated ultrasound device, the image frame comprising an x-axis that is substantially parallel to a length of the cardiac vessel and a y-axis that is perpendicular to the x-axis;

applying a median filter iteratively to pixels within the ROI;

determining a shift between intensity vectors corresponding to neighboring or adjacent X coordinates;

determining a Running Pattern (RP) and an Inversed Running Pattern (IRP) for each of the X coordinates within the ROI; and outputting to a display at least one indication of a location of a layer within the cardiac vessel, the location based at least on the RP and the IRP.

35. A method in accordance with claim 34, further comprising:
   wherein the determining the RP and IRP further comprises determining, for each of the X coordinates, a Running Shift (RS) between the intensity vector and the RP corresponding to a current X coordinate and an Averaged Shift (AS) between the intensity vector corresponding to the current X coordinate and an Averaged Pattern (AP); and
   determining, for each of the X coordinates, a Y coordinate of a layer within the vessel based on at least one of the RS and the AS.

36. A method in accordance with claim 34, further comprising determining a Y coordinate of the intima-media center based on at least one of an Averaged Pattern (AP) and an Inversed Averaged Pattern (IAP), wherein the AP and the IAP are based on an average along the x-axis of all intensity vectors into the ROI.

37. A method in accordance with claim 34, wherein the location being further based on:
   determining an Averaged Pattern (AP) and an Inversed Averaged Pattern (IAP) using an average along the x-axis of all intensity vectors into the ROI, taking into account shift between the neighbor vectors wherein the AP is evaluated in the ascending direction of the x-axis and the IAP is evaluated in the descending direction of the x-axis;
   determining a shift between the AP and the first vector in the ROI using a maximum of a cross correlation function between the AP with the first vector in the ROI; and
   determining a shift between the IAP and the last vector in the ROI using a maximum of a cross correlation function between the IAP with the last vector in the ROI.

38. A method in accordance with claim 37, further comprising determining the Y coordinate of the IMC as a maximum of a second derivative of AP/IAP.

39. A method in accordance with claim 34, wherein the shift between the intensity vectors is further determined using a maximum of a cross correlation function, calculated for each of the X coordinates within the ROI.

40. A method in accordance with claim 34, wherein the RP and the IRP are calculated for each of the X coordinates as an average along the x-axis of the intensity vectors inside a window, taking into account shift between neighbor vectors, the RP being evaluated in an ascending direction of the x-axis, the IRP being evaluated in the descending direction of the x-axis.

41. A method in accordance with claim 34, wherein the location indicating at least one of an intima-media center (IMC), an adventitia-media interface, an intima-lumen interface, and a media-adventitia interface.

42. A method in accordance with claim 6, wherein the multi-layer cardiac vessel comprises one of a carotid artery, a coronary artery and an aorta.

43. An integrated ultrasound device in accordance with claim 19, wherein the cardiac vessel comprises one of a carotid artery, a coronary artery and an aorta.

44. A method in accordance with claim 34, wherein the multi-layer cardiac vessel comprises one of a carotid artery, a coronary artery and an aorta.

* * * * *